(12) United States Patent
De Smedt et al.

(10) Patent No.: US 8,939,376 B1
(45) Date of Patent: Jan. 27, 2015

(54) ENCODING OF MICROCARRIERS

(75) Inventors: Stefaan Cornelis De Smedt, Ghent (BE); Joseph Demeester, Ghent (BE); Christiaan Hubert Simon Roelant, Leuven (BE); Rudi Wilfried Jan Pauwels, Bonheiden (BE)

(73) Assignee: Mycartis NV, Zwijnaarde / Ghent (BE)

( * ) Notice: Subject to any disclaimer, the term of this patent is extended or adjusted under 35 U.S.C. 154(b) by 1826 days.

(21) Appl. No.: 09/958,655

(22) PCT Filed: Apr. 12, 2000

(86) PCT No.: PCT/EP00/03280
§ 371 (c)(1),
(2), (4) Date: Jan. 9, 2002

(87) PCT Pub. No.: WO00/03695
PCT Pub. Date: Oct. 20, 2000

Related U.S. Application Data (60) Provisional application No. 60/129,551, filed on Apr. 16, 1999.

(51) Int. Cl.
*G06K 19/00* (2006.01)

(52) U.S. Cl.
USPC .......................................... 235/487; 235/494

(58) Field of Classification Search
USPC ............... 235/487, 375, 494, 462.01, 462.06
See application file for complete search history.

(56) References Cited

U.S. PATENT DOCUMENTS

| | | | | |
|---|---|---|---|---|
| 3,786,237 A | * | 1/1974 | Postal | 235/491 |
| 4,390,452 A | * | 6/1983 | Stevens | 235/408.1 |
| 5,129,974 A | * | 7/1992 | Aurnius | 235/462.01 |
| 5,492,222 A | * | 2/1996 | Weaver | 235/487 |
| 5,565,324 A | | 10/1996 | Still et al. | |
| 5,721,099 A | | 2/1998 | Still et al. | |
| 5,736,332 A | | 4/1998 | Mandecki | |
| 5,751,629 A | | 5/1998 | Nova et al. | |
| 5,789,172 A | | 8/1998 | Still et al. | |
| 5,896,403 A | * | 4/1999 | Nagasaki et al. | 714/752 |
| 6,023,540 A | * | 2/2000 | Walt et al. | 385/12 |
| 6,214,618 B1 | | 4/2001 | Hillegas et al. | |

(Continued)

FOREIGN PATENT DOCUMENTS

| | | | | |
|---|---|---|---|---|
| GB | 2306484 | | 5/1997 | |
| JP | 62-032896 | * | 2/1987 | C12P 21/00 |

(Continued)

OTHER PUBLICATIONS

Braeckmans, K. et al., "Encoding Microcarriers: Present and Future Technologies", *Nature Reviews/Drug Discovery*, 2002, 1, 11 pages.

(Continued)

*Primary Examiner* — Daniel St Cyr
(74) *Attorney, Agent, or Firm* — Kusner & Jaffe (57) ABSTRACT

Encoded microcarriers, and more specifically microcarriers having codes written on them. Methods for writing the codes on the microcarriers, methods of reading the codes, and methods of using the encoded microcarriers. A preferred method of encoding the microcarriers involves exposing microcarriers containing a bleachable substance to a high spatial resolution light source to bleach the codes on the microcarriers. The encoded microcarriers may be used, for example, as support materials in chemical and biological assays and syntheses.

11 Claims, 8 Drawing Sheets

(56) References Cited

U.S. PATENT DOCUMENTS

| | | | |
|---|---|---|---|
| 6,329,139 B1 * | 12/2001 | Nova et al. | 435/6 |
| 6,350,620 B2 * | 2/2002 | Chang et al. | 436/518 |
| 6,458,165 B1 * | 10/2002 | Foucher et al. | 235/487 |
| 6,461,690 B2 * | 10/2002 | Corbett | 427/511 |
| 6,841,147 B2 | 1/2005 | Zsebo et al. | |
| 6,844,170 B1 | 1/2005 | Moore et al. | |
| 6,908,737 B2 * | 6/2005 | Ravkin et al. | 435/6 |
| 7,350,711 B2 * | 4/2008 | He et al. | 235/462.2 |
| 2002/0084329 A1 | 7/2002 | Kaye et al. | |
| 2004/0069857 A1 * | 4/2004 | Leblans et al. | 235/494 |

FOREIGN PATENT DOCUMENTS

| | | | | |
|---|---|---|---|---|
| WO | 95/29473 | | 11/1995 | |
| WO | 97/12680 | | 4/1997 | |
| WO | 97/15390 | | 5/1997 | |
| WO | WO 98/40726 | | 9/1998 | |
| WO | WO 98/53093 | | 11/1998 | |
| WO | WO 99/18434 | | 4/1999 | |
| WO | WO 99/19344 | | 4/1999 | |
| WO | WO 99/19515 | | 4/1999 | |
| WO | WO 99/24458 | | 5/1999 | |
| WO | WO 99/37814 | | 7/1999 | |
| WO | 00/16893 | * | 3/2000 | B01J 19/00 |
| WO | 0233419 | * | 4/2002 | G01N 33/58 |

OTHER PUBLICATIONS

Burgess, D.S., "Photobleaching Offers Coded Microspheres", *Photonics Spectra*, May 2003, 27, 3 pages.

Wedekind, P. et al., "Line-Scanning Microphotolysis for Diffraction-Limited Measurements of Lateral Diffusion", *Biophysical Journal*, 1996, 71, 1621-1632.

Wedekind et al., "Scanning microphotolysis: a new photobleaching technique based on fast intensity modulation of a scanned laser beam and confocal imaging", Journal of Microscopy, pp. 23-33, vol. 176, pt. 1, Oct. 1994.

Philippe Gribbon et al., "Macromolecular Diffusion of Biological Polymers Measured by Confocal Fluorescence Recovery after Photobleaching", Biophys J., vol. 75, No. 2, pp. 1032-1039, Aug. 1998.

S. C. De Smedt et al., "Diffusion of Macromolecules in Dextran Methacrylate Solutions and Gels As Studied by Confocal Scanning Laser Mircoscopy", Marcomolecules, vol. 30, pp. 4863-4870 (1997).

S. C. De Smedt et al., "Structural Information on Hyaluronic Acid Solutions As Studied by Probe Diffusion Experiments", Macromolecules, vol. 27, pp. 141-146 (1994).

U. Kubitscheck et al., "Two-photon scanning microphotolysis for three-dimensional data storage and biological transport measurements", Journal of Microscopy, vol. 182, pt. 3, pp. 225-233, Jun. 1996.

J. C. C. Blonk et al., "Fluorescence photobleaching recovery in the confocal scanning light microscope", Journal of Microscopy, vol. 169, pt. 3, pp. 363-374, Mar. 1993.

D. A. Berk et al., "Fluorescence Photobleaching with Spatial Fourier Analysis: Measurement of Diffusion in Light-Scattering Media", Biophysical Journal, vol. 65, pp. 2428-2436, Dec. 1993.

Reiner Peters et al., "Fluorescence Photobleaching Techniques", New Techniques of Optical Mircoscopy and Microspectroscopy, vol. 8, pp. 199-228.

Peter Wedekind et al., "Line-Scanning Microphotolysis for Diffraction-Limited Measurements of Lateral Diffusion", Biophysical Journal, vol. 71, pp. 1621-132, Sep. 1996.

W. N. E. Van Dijk-Wolthuis et al., "Reaction of Dextran with Glycidyl Methacrylate : An Unexpected Transesterification", Macromolecules, vol. 30, pp. 3411-3413 (1997).

Robert J. H. Stenekes et al., "The Preparation of Dextral Microspheres in an All-Aqueous System: Effect of the Formulation Parameters on Particle Characteristics", Pharmaceutical Research, vol. 15, No. 4, pp. 557-561 (1998).

Eric Neil Kaufman et al., "Measurement of mass transport and reaction parameters in bulk solution using photobleaching", Biophys. J. Biophysical Society, vol. 60, pp. 596-610, Sep. 1991.

Ulrich Kubitscheck et al., "Single Nuclear Pores Visualized by Confocal Microscopy and Image Processing", Biophysical Journal, vol. 70, pp. 2067-2077, May 1996.

Eric Poitevin et al., "Study of the translation diffusion of macromolecules in beads of gel chromatography by the FRAP method", Biophysical Chemistry, vol. 31, pp. 247-258 (1988).

Richard J. Cherry et al., "New Techniques of Optical Microscopy and Microspectroscopy", Library of Congress Cataloging-in-Publication Data, vol. 8, pp. 199-228 (1990).

* cited by examiner

ENCODING OF MICROCARRIERS

This application is a national stage filing under 35. U.S.C. §371 of international application no. PCT/EP00/03280, filed on Apr. 12, 2000, which published in the English language. This application also claims priority benefit to U.S. provisional application Ser. No. 60/129,551, filed on Apr. 16, 1999. The content of the provisional application is incorporated by reference herein.

FIELD OF THE INVENTION

This invention relates to encoded microcarriers, and more specifically to microcarriers having codes written on them. Any reference in this disclosure to codes written "on" the microcarriers includes codes written on the surface of the microcarriers as well as codes written at an internal depth of the microcarriers. This invention also relates to methods for writing codes on microcarriers, methods of reading the codes, and methods of using the encoded microcarriers. A preferred method of encoding the microcarriers involves exposing microcarriers that carry a bleachable substance to a high spatial resolution light source to bleach the codes on the microcarriers. The encoded microcarriers may be used, for example, as support materials in chemical and biological assays and syntheses.

DESCRIPTION OF THE RELATED ART

Drug discovery and drug screening in the chemical and biological arts commonly involve performing assays on very large numbers of compounds or molecules. These assays typically include screening chemical libraries for compounds of interest, screening for particular target molecules in test samples, and testing generally for chemical and biological interactions of interest between molecules. The assays described above often require carrying out thousands of individual chemical or biological reactions. For example, a drug discovery assay may involve testing thousands of compounds against a specific target analyte. Any compounds that are observed to react, bind, or otherwise interact with the target analyte may hold promise for any number of utilities where the observed interaction is believed to be of significance.

A number of practical problems exist in the handling of the large number of individual reactions required in the assays described above. Perhaps the most significant problem is the necessity to label and track each reaction. For example, if a reaction of interest is observed in only one in a group of thousands of reactions, the researcher must be able to determine which one of the thousands of initial compounds or molecules produced that reaction.

One conventional method of tracking the identity of the reactions is by physically separating each reaction into an individual reaction vessel within a high-density array and maintaining a record of what individual reactants were used in each vessel. Thus, for example, when a reaction of interest is observed in a vessel labeled as number 5 of 1000, the researcher can refer to the record of reactants used in the vessels and will learn from the record of vessel 5 what specific reactants were present to lead to the reaction of interest. Examples of the high-density arrays referred to above are 384-, 864-, 1,536-, 3,456-, and 9,600-well microtiter plate containers, where each well of a microtiter plate constitutes a miniature reaction vessel. Miniaturized reaction wells are used because they conserve space and reduce the cost of reagents used in the assays.

The use of microtiter plate containers in chemical and biological assays, however, carries a number of disadvantages. For example, the use of the plates requires carefully separating a very large number of discrete reaction vessels, rather than allowing for all reactions to take place freely, and often more conveniently, in one reaction vessel. Furthermore, the requirement that the reaction volumes be spatially separated carries with it a physical limitation to the size of microtiter plate used, and thus to the number of different, reactions that may be carried out on the plate.

In light of the limitations described above in the use of microliter plates, some attempts have been made to develop other means of tracking individual reactions in high-throughput assays. These methods have abandoned the concept of spatially separating the reactions, and instead track the individual reactions by other means. For example, methods have been developed to carry out high-throughput assays and reactions on microcarriers as supports. Each microcarrier may contain one particular ligand bound to its surface to act as a reactant, and the microcarrier can additionally contain a "code" that identifies the microcarrier and therefore identifies the particular ligand bound to its surface. These methods described above allow for "random processing," which means that thousands of uniquely coded microcarriers, each having a ligand bound to their surface, may all be mixed and subjected to an assay simultaneously. Those microcarriers that show a favorable reaction of interest between the attached ligand and target analyte may then have their code read, thereby leading to the identity of the ligand that produced the favorable reaction.

The practice of random processing described above requires accurate encoding of each of the microcarriers separately, and requires accurate and consistent identification of the codes. Because assays using random processing rely heavily on the coding of the microcarriers for their results, the quality of the assays depends largely on the quality and readability of the codes on the microcarriers. Attempts to code microcarriers are still limited to differential coloring (Dye-Trak microspheres), fluorescent labeling (Fluorospheres; Nu-flow), so-called remotely programmable matrices with memories (IRORI; U.S. Pat. No. 5,751,629), detachable tags such as oligonucleotides and small peptides (U.S. Pat. No. 5,565,324; U.S. Pat. No. 5,721,099; U.S. Pat. No. 5,789,172), and solid phase particles that carry transponders (U.S. Pat. No. 5,736,332). The disclosures of the patents cited above are incorporated by reference herein.

These known methods identified above for coding microcarriers each carry disadvantages. For example, microcarriers that are differentiated solely on the basis of their size, shape, color, fluorescence intensity, or combinations thereof often cannot provide enough unique readable combinations of those variables to create the massive number of unique codes necessary to accompany the testing of a correspondingly large number of different molecules. In addition, any microcarriers carrying foreign bodies on their surface to serve as the codes, such as detachable tags or fluorescent markers, run the risk that the attached moieties may interfere with the binding or reaction of the ligand-bound molecules on the microcarriers that target the analytes in the assays. After the separation of the microcarriers of interest that exhibit a favorable reaction, methods of encoding microcarriers with detachable tags also often involve the additional step of cleaving and analyzing the tags to ultimately learn the identity of the underlying ligands on the microcarriers that produced the favorable reactions. This cleaving step naturally extends the time and effort necessary to determine the results of the tests.

In light of the above, there remains in the art a need for simple ways for identifying single microcarriers in a massive population of otherwise identical microcarriers, especially ways for encoding a larger number of unique codes that need not be attached as foreign bodies to the surfaces of the microcarriers.

SUMMARY OF THE INVENTION

An object of the invention is to provide a microcarrier that is encoded without the need for attaching a foreign object to the surface of the microcarrier to serve as the code. Another object of the present invention is to provide a method of encoding microcarriers that may provide essentially unlimited possibilities as to the varieties of unique codes that may be written and read on the microcarriers.

The present invention fulfills these objectives by providing microcarriers having codes written on them. Preferred microcarriers are microcarriers containing bleachable substances, for example, fluorescent molecules. A preferred method of encoding the microcarriers involves exposing microcarriers carrying a bleachable substance to a high spatial resolution light source to bleach the codes on the microcarriers. This method may preferably involve bleaching codes on fluorescent microcarriers, where the bleaching produces either the same or different levels of fluorescent intensity within the bleached portions of the code. A further preferred method of encoding the microcarriers is writing the codes at an internal depth of the microcarriers.

In another preferred embodiment, large numbers of chemical compounds or biological molecules are bound to a correspondingly large number of microcarriers of the invention, the microcarrier-bound ligands are mixed and reacted simultaneously according to a screening or assay protocol, and those ligands that react are identified by reading the code on the microcarriers to which they are bound.

The encoded microspheres of the invention allow for the simultaneous analysis of a large number of analytes in a single reaction vessel using a single sample aliquot. Use of the microcarriers of the invention in high-throughput assays and reactions is therefore far superior compared to the use of conventional microtiter plate technology.

The microcarriers of the invention also provide a virtually unlimited number of codes that may be written and read on the microspheres, and are therefore superior to known microcarriers coded with color or fluorescent tags, which carry a more limited number of coding possibilities. The microcarriers of the invention are also superior to microcarriers coded with moieties attached to the surfaces of microcarriers. This is because the writings on the microcarriers of the invention do not carry the risk associated with those known microcarriers of potentially interfering with the analyte/ligand interactions that take place on the surfaces of the microcarriers.

Additional features and advantages of the invention are set forth in the description that follows, and in part will be apparent from the description or may be learned from practice of the invention. The advantages of the invention will be realized and attained by the encoded microcarriers and methods particularly pointed out in the written description and claims. Both the foregoing general description and the following detailed description of the invention are exemplary and explanatory only and are not restrictive of the claimed invention.

BRIEF DESCRIPTION OF THE DRAWINGS

FIG. 10a illustrates confocal images of codes bleached to different intensities, and FIGS. 10b to 10d graphically illustrate the different intensities within the codes.

FIGS. 11a and 12a illustrate confocal images of codes bleached to different intensities, and FIGS. 11b and 12b graphically illustrate the different intensities within the respective codes.

DETAILED DESCRIPTION OF THE INVENTION

In one embodiment, the present invention relates to microcarriers having codes written on them. The microcarriers of the invention may be made from, for example, any materials that are routinely used in high-throughput screening technology and diagnostics. For example, the microcarriers may be made from a solid, a semi-solid, or a combination of a solid and a semi-solid. Non-limiting examples of these materials include latex, polystyrene, cross-linked dextrans, methylstyrene, polycarbonate, polypropylene, cellulose, polyacrylamide, and dimethylacrylamide. Preferred materials include latex, polystyrene, and cross-linked dextrans. The microcarriers may also be prokaryotic or eukaryotic cells.

The microcarriers may be of any shapes and sizes that lend themselves to the encoding and use of the microcarriers. For example, the microcarriers may be in the form of spheres, or in the form of beads that are not necessarily spherical. The microcarriers may be, for example, cylindrical or oval in shape. When spherical in shape, the microcarriers may have, for example, a diameter of 1 to 200 µm.

The codes written on the microcarriers may be of any geometry, design, or symbol that can be written and read on the microcarriers. For example, the codes may be written as numbers or letters, or as codes in the form of symbols, pictures, bar codes, ring codes, or three-dimensional codes. Ring codes are similar to bar codes, except that concentric circles are used rather than straight lines. A ring may contain, for example, the same information as one bar. The codes may be written on the surface of the microcarriers or at an internal depth of the microcarriers. For example, the codes may be written at an internal depth of the microcarriers, and more particularly in the center plane of the microcarriers. Depending on the shape of the microcarriers, the center plane may be a preferable location for writing the code because it may provide the largest surface area available for writing. Furthermore, for microcarriers having curved surfaces, it may be more advantageous to write the codes at an internal depth rather than on the curved surfaces. This is because it may often be more convenient to write and read the codes on a flat plane rather than on a curved surface.

The microcarriers of the invention may contain a bleachable substance, and the codes on the microcarriers may be in the form of bleached patterns within the bleachable portions of the microcarriers. The microcarriers may contain the bleachable substance either on the surface of the microcarrier or also within the body of the microcarrier. Any reference in this application to the bleaching of substances "on" the microcarriers includes bleaching at the surface of the microcarrier as well as bleaching at an internal depth of the microcarriers. Preferred bleachable substances include bleachable fluorescent or electromagnetic radiation absorbing substances. The microcarriers may contain bleachable luminophores. Examples of luminophores that can be used include fluorescers, phosphorescers, or scintillators. Bleachable chemiluminescent, bioluminescent, or colored substances may be used. The bleachable substances may be, more specifically, fluorescein isothiocyanate ("FITC"), phycoerythrines, coumarins, lucifer yellow, and rhodamine. The bleachable substances should be chosen so that, when bleaching occurs, the code remains on the microcarrier for the period of time that is desired for the use of the microcarriers and any necessary reading of the codes. Thus, a certain amount of diffusion of non-bleached molecules into the bleached areas is acceptable as long as the useful life of the code is preserved.

Codes bleached on microcarriers may also be written to have different intensities of fluorescence or color within bleached areas of the microcarriers. For example, a bleached coding may contain several different degrees of bleaching, thereby having several different intensities of fluorescence within the bleached region as a whole. Thus, microcarriers may be encoded not only by the geometry of the pattern bleached on the microcarriers, but also by the use of different fluorescent intensities within the pattern.

In another embodiment, the invention relates to a method for writing codes on microcarriers. The method may be used to write the codes either on the surfaces of the microcarriers or at an internal depth of the microcarriers. The codes can be written on the microcarriers, for example, by using a high spatial resolution light source, such as a laser, a lamp, or a source that emits X-rays, α and β rays, ion beams, or any form of electromagnetic radiation. The codes can also be written on the microcarriers through photochroming or chemical etching. A preferred method for writing the codes is through the use of a high spatial resolution light source, and in particular a laser or a lamp in combination with a confocal microscope. Another preferred method for writing the codes is by bleaching the code in a bleachable substance on the microcarrier. Preferred bleachable substances in this method include those substances identified above in the description of the microcarriers, and include fluorescent molecules. With regard to the volume of material that may be bleached within the microcarriers, one example of such a volume is between one cubic nanometer and eight cubic millimeters of the microcarrier.

One preferred method for writing the codes on the microcarriers is through the use of scanning microphotolysis ("SCAMP"). The technical features of SCAMP were first described in P. Wedekind at al., "Scanning microphotolysis: a new photobleaching technique based on fast intensity modulation of a scanned laser beam and confocal imaging," Journal of Microscopy, vol. 176, pp. 23-32 (1994), the content of which is incorporated by reference herein. The above article discloses the use of SCAMP for the bleaching and visualization of patterns in a thin fluorescent layer of nail polish. The article does not suggest the use of SCAMP for encoding microcarriers.

We have used SCAMP for writing codes on the microcarriers by bleaching fluorescent molecules within the microcarriers. Photobleaching is a well-known phenomenon referring to the fading of colors due to the fact that certain wavelengths of light when shone on a given pigment will cause the pigment's molecules to resonate and eventually break down. This is also the reason why fluorescent molecules often tend to bleach when excited by a powerful laser beam of specific wavelength.

For many years, fluorescence microphotolysis ("MP") techniques, also called fluorescence recovery after photobleaching ("FRAP") were used to study the mobility of fluorescent molecules in both biological media, like cells and tissues, and non-biological media. Peters and Scholtz, "Fluorescence photobleaching techniques," in New Techniques of Optical Microscopy and Microspectroscopy, R. J. Cherry (ed.), MacMillan, New York, pp. 199-228 (1991); De Smedt et al., "Structural Information on Hyaluronic Acid Solutions as Studied by Probe Diffusion Experiments," Macromolecules, vol. 27, pp. 141-146 (1994); De Smedt et al., "Diffusion of Macromolecules in Dextran Methacrylate Solutions and Gels as Studied by Confocal Scanning Laser Microscopy," Macromolecules, vol. 30, pp. 4863-4870 (1997).

Figure 1:
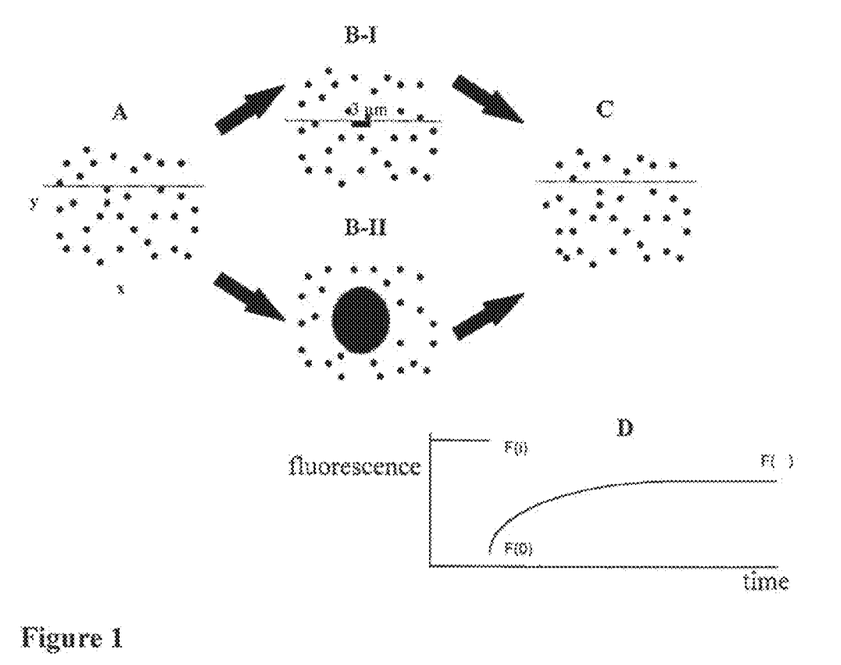
FIG. 1 illustrates a number of principles of conventional microphotolysis and SCAMP.

The mobility of fluorescent molecules can be measured by bleaching (photolyzing) the fluorescent molecules moving in the focal area of a light beam, which can be particularly a laser beam (FIG. 1: A, B). Immediately after a short bleaching process, typically about ten milliseconds, a highly attenuated laser beam measures the recovery of the fluorescence in the photobleached area due to the diffusion of fluorescent molecules from the surrounding unbleached areas into the bleached area (FIG. 1: B, C). The characteristic diffusion time, a measure for the diffusion coefficient and the fractions of respectively immobile and mobile fluorescent molecules can be derived from the fluorescence recovery in the bleached area (FIG. 1: D).

The mobile fraction, R, is defined as:

$$R = \frac{F(\infty) - F(0)}{F(i) - F(0)},$$

where F(i) is the fluorescence intensity of the bleach spot before bleaching, F(0) is fluorescence intensity of the bleach spot just after bleaching and F(∞) is the fluorescence intensity of the bleach spot at a long time after bleaching.

In photobleaching experiments using a conventional (non-scanning) light microscope, a stationary (laser) light beam is focused on the sample during both the bleaching process as well as the recovery period. The stationary position of the (laser) light beam during the bleaching process results in a photobleached area that has a circular geometry. Although non-scanning light microscopes technically yield an irradiated area of 2 µm or less in diameter, broadening of the bleach spot often occurs due to the stationary laser beam. This results in large circular bleached spots that are typically 10 µm-20 µm in diameter or even larger, as schematically illustrated in FIG. 1: B-II.

The availability of laser light scanning microscopes opened new opportunities for microphotolysis methods. The combination of photolysis, beam scanning, and confocal microscopy lead to the development of SCAMP. In SCAMP, bleaching occurs during scanning a sample by switching between low monitoring and high photobleaching laser intensity levels in less than a microsecond using an intensity modulation device such as an acousto-optical modulator ("AOM"). The combination of bleaching during scanning and the use of the AOM, which generates extremely short bleaching pulses, prevents the broadening of the bleach spot that occurs in conventional microphotolysis due to longer photobleaching times and the stationary laser beam. SCAMP allows for bleaching spots of less than a micrometer in the sample.

FIG. 1 illustrates schematically how SCAMP proceeds to measure the mobility of fluorescent molecules. First, the fluorescence along one x-line of the plane of interest in the sample is measured by scanning this line (FIG. 1: A-dotted line). Second, a small segment (e.g. 3 μm) on this x-line, in which diffusion has to be investigated, is selected to be bleached (FIG. 1: B-I). The length, position, as well as the number of segments are freely selectable by the SCAMP software. The photobleaching of this segment occurs at the time the laser beam scans over this segment accompanied by a temporarily strong increase in the intensity of the laser beam. Typically, the ratio between photobleaching and monitoring intensity levels of the laser beam is larger than 100.

As SCAMP makes use of a confocal microscope, fluorescence detection is not only allowed at the surface of the sample, but also at an arbitrary depth in the sample with little interference by scattered radiation from out-of-focus levels of the specimen (as encountered in a conventional microscope). In contrast, when a fluorescence lamp for illumination and a conventional (non-focal) microscope is used, only the surface of the beads is typically observed. An encoding at an internal depth is therefore generally difficult to observe with an ordinary microscope but becomes well visible with confocal optics. Both the confocal and scanning features of the microscope allow photolyzing and reading microregions at well-defined locations within a microcarrier. This invention is clearly distinguished from all other applications described thus far in the art in that, for example, the use of a high spatial resolution of SCAMP can irreversibly mark microspheres inside at specific depths and to read that encoding by confocal techniques.

Figure 2A:
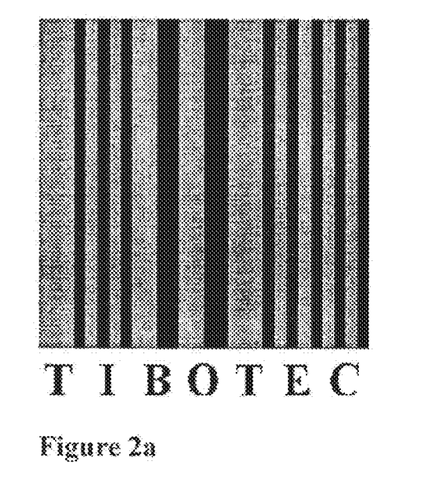
FIGS. 2a and 2b illustrate a bar code and ring code using different intensities, with each intensity being denoted by the different colors shown in the Figures.
Figure 2B:
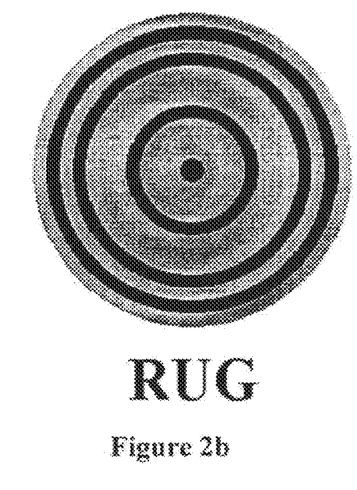

The methods of the invention for writing codes on microcarriers may also involve bleaching the microcarriers to produce different levels of intensity in the substances bleached in the code. In addition to conveying the information in the design of the code itself, information can also be conveyed by different intensities within the bleached patterns. The ability to encode the microcarriers with different intensities may permit smaller codes on the microcarriers, thus saving space, but still conveying the same number or more of unique identifiers to code microcarriers. As an example, it is possible according to the invention to bleach four different intensities in the beads. This can be accomplished in a number of ways, for example, by repeated bleaching over some portions of the bead relative to others, or by dissipating different levels of acoustic power into an AOM to produce a plurality of different laser powers that will create bleached patterns having different intensities based on the power of laser light used for each portion of the code. FIGS. 2a and 2b are two examples of codes bleached using different intensities, one with a bar pattern, the other with a ring pattern. The different intensities in the codes are represented by different colors in the Figures. Different levels of intensity can also be combined with different breadths of the coding elements, such as bars in bar codes.

Another embodiment of the invention relates to reading the codes on the encoded microspheres of the invention. Reading of the codes may be performed with an ordinary microscope if the code is on the surface of the microcarrier or, if the microcarrier is sufficiently translucent, at an internal depth of the microcarrier. Reading of the codes may also be performed using a confocal microscope. In particular, the codes may be read by suspending the microcarriers in an aqueous environment, placing the microcarriers between two glass slides or placing them in microcapillaries, and observing the codes through a microscope or confocal microscope.

Another embodiment of the invention relates to methods of using the encoded microspheres of the invention. The microcarriers may be used as supports for the measurement of biomolecular interactions, for drug discovery, receptor binding assays, therapeutics, medical diagnostics, combinatorial chemistry, isolation and purification of target molecules, capture and detection of macromolecules for analytical purposes, selective removal of contaminants, enzymatic catalysis, chemical modification, hybridization reactions and forensic applications.

The microcarriers may preferably serve as supports for chemical and biological assays and syntheses. In this capacity, the microcarriers may contain one or more ligands bound to the surface of the microcarriers. The ligand-bound microcarriers may then be contacted with target analytes to determine the presence or absence of particular analytes of interest, or may serve as supports for combinatorial chemistry reactions performed on the microcarrier-bound ligand. Examples of target analytes for the microcarrier-bound ligands include antigens, antibodies, receptors, haptens, enzymes, proteins, peptides, nucleic acids, drugs, hormones, pathogens, toxins, or any other chemicals or molecules of interest. Whether or not a microcarrier-bound ligand binds or reacts with a target analyte may be determined by conventional techniques used in the art for that determination. For example, the reaction may be indicated by a luminometric response. The reaction may be indicated by a colorimetric, chemiluminometric, or fluorinometric response. The ligand bound to the microcarrier of interest may be designed so that, in the presence of the analytes of interest to which it is targeted, an optical signature of the microsphere is changed. For example, such a change in optical signature may be the result of a photochemical reaction that occurs when the binding or reaction takes place between the ligand and analyte. The microcarriers may then be observed under the microscope to detect a fluorescence associated with the photochemical reaction.

A large spectrum of chemical and biological functionalities may be attached as ligands to the microcarriers of the invention. These functionalities include all functionalities that are routinely used in high-throughput screening technology and diagnostics. The ligands may be attached to the microcarriers by means conventionally used for attaching ligands to microcarriers in general, including by means of a covalent bound and through direct attachment or attachment through a linker. Furthermore, the microcarriers can be functionalized in a variety of ways to allow attachment fan initial reactant.

The microcarriers of the invention may be used in methods of detecting the presence or absence of one or more target analytes in a sample, which comprise contacting a microcarrier-bound ligand with at least one analyte, detecting whether the analyte has reacted or bound to the ligand, and reading the code of any microcarrier upon which any reaction or binding has occurred.

More specifically, the invention relates to a method of detecting the presence or absence of one or more target analytes in a sample, which comprises choosing one or more ligands which bind or react with the one or more analytes, binding the ligands to a plurality of microcarriers of the invention, correlating the identity of the ligands with the codes on the microcarriers to which the ligands are bound, contacting the one or more analytes with the ligand-bound microcarriers, observing any microcarriers upon which the analyte has bound or reacted with the microcarrier-bound ligand, and reading the codes on the microcarriers to identify any ligands with which the one or more analytes have reacted, thereby determining the presence or absence of the one or more analytes.

A preferred embodiment of the above method is where the target analyte is a nucleic acid, particularly DNA or RNA, and wherein at least one microcarrier-bound ligand is the reverse compliment of the nucleic acid. The microcarriers of the invention are thus useful in DNA hybridization. The microcarriers are also useful for enzyme-based assays and immunoassays. The microcarriers may also be used in assays conducted to screen for certain compounds in samples, and also for detecting and isolating compounds from those samples. The microcarriers may also be used as supports for creating or for reacting members of a combinatorial chemistry library.

The microcarriers of the invention may also be used in methods and devices employed for the efficient and rapid screening of large numbers of components, where the variety may be in either or both of a ligand bound to a microcarrier or a soluble analyte component, where one is interested in determining the occurrence of an interaction between the two components. The devices include a microarray such as, for instance, a solid support upon which the bound ligands have been placed in a predetermined registry and a reader for detecting the interaction between the components. The method may involve preparing the microarray such as, for instance, the solid support for attachment of the ligand, then combining the ligand and analyte to effect any interaction between the components and subsequently determining the presence of an interaction between the components and particular sites.

The microarray will normally involve a plurality of different components. In theory there need by only one component, but there may be as many as $10^5$. While the number of components will usually not exceed $10^5$, the number of individual encoded microcarriers may be substantially larger.

The bound ligand may for instance be an organic entity, such as a single molecule or assemblages of molecules, ligands and receptors, nucleic acid bound components, RNA, single strand and double strand binding proteins, which do not require that there be a binding ligand attached to the nucleic acid, oligonucleotides, proteins.

The encoded microcarriers in the microarray may be arranged in tracks. Headers are provided for defining sites, so that particular interactions can be rapidly detected. Particularly, disks having circular tracks with headers defining sites on the tracks, so that positive signals can be interpreted in relation to the information provided by the header. The circular tracks are preferably concentric and have a cross-section in the range of 5 to 5000 μm. Various modifications are possible, such as pre-prepared segments which may then be attached to the disk for assaying.

The present invention is further illustrated by the following examples that further teach those of ordinary skill in the art how to practice the invention. The following examples are merely illustrative of the invention and disclose various beneficial properties of certain embodiments of the invention. The following examples should not be construed as limiting the invention as claimed.

Example 1

Dextran-methacrylate ("dex-ma"), used to prepare dex-ma microspheres, was synthesized and characterized as described in detail in W. N. E. van Dijk-Wolthius et al, "Reaction of Dextran with Glycidyl Methacrylate; An Unexpected Tnmsesterification," Macromolecules, vol. 30, pp. 3411 to 3413 (1997), the disclosure of which is incorporated by reference herein. Dex ma microspheres were prepared by radical polymerization, using N,N,N',N'-tetramethylene-ethylenediamine and potassium persulfate, from a dex-ma/polyethyleneglycol (PEG) emulsion. See Stenekes et al., "The Preparation of Dextran Microspheres in an All-Aqueous System: Effect of the Formulation Parameters on Particle Characteristics," Pharmaceutical Research, vol. 15, pp. 557-561 (1998), the disclosure of which is incorporated by reference herein. The concentration of the dex-ma solution (m phosphate buffer at pH 7) was 10% (w/w). The degree of substitution of dex-ma, being the number of methacrylate molecules per 100 glycopyranosyl units, was 4. The concentration of PEG solution in phosphate buffer at pH 7 was 24% w/w, while the average molecular weight of PEG was 10,000 g/mol (Merck). One batch of microspheres (FD148-dex-ma microspheres) was prepared in the presence of fluorescein isothiocyanate labeled dextral (having a molecular weight of 148.000 g/mol). A second batch of microspheres was loaded with fluorescein isothiocyanate ("FITC") by submersion of the dex-ma microspheres, after complete preparation, in an FITC solution (0.01 mg/ml in phosphate buffer at pH 7.2). Both FD148 and FITC were obtained from Sigma. SCAMP experiments were performed on both batches of microspheres as explained in Example 2.

Example 2

SCAMP was installed on a Bio-Rad MRC1024 confocal laser scanning microscope ("CLSM") following of the work of Wedekind et al., "Seaming microphotolysis: a new photobleaching technique based on fast intensity modulation of a scanned laser beam and confocal imaging," Journal of Microscopy, vol. 176, pp. 23-32 (1994) and Wedekind et al., "Line-Scanning Microphotolysis for Diffraction-Limited Measurements of Lateral Diffusion," Biophysical Journal, vol. 71, pp. 1621-1632 (1996), the disclosures of which are incorporated by reference herein. A 40× oil immersion objective and a powerful 2 W (representing the maximum possible output) argon laser (Spectra Physics 2017), used for obtaining sufficient photobleaching during the extremely short photobleaching times, were used in the SCAMP experiments on the dex-ma microspheres made according to Example 1. The wavelength of the laser beam, also during bleaching, was 488 nm.

In this example, SCAMP experiments were performed at approximately 10 μm below the surface of the dex-ma microspheres. It occurred experimentally as follows. First, the fluorescence along one x-line of a middle plane of a dex-ma microsphere was measured by scanning this line in 400 milliseconds (FIG. 1: A-dotted line). Second, a 3 μm segment on this x-line was selected to be bleached (FIG. 1: B-I). The length, position, as well as the number of segments are freely selectable by the SCAMP software. The photobleaching of this segment occurred at the time the laser beam scanned over this segment accompanied by a temporarily strong increase in the intensity of the laser beam. The ratio between monitoring and photobleaching intensity levels of the laser beam was 1:500. To measure the fluorescence recovery in the bleached stripe, a strongly attenuated laser beam scanned along the selected x-line for approximately 4 seconds.

Figure 3A:
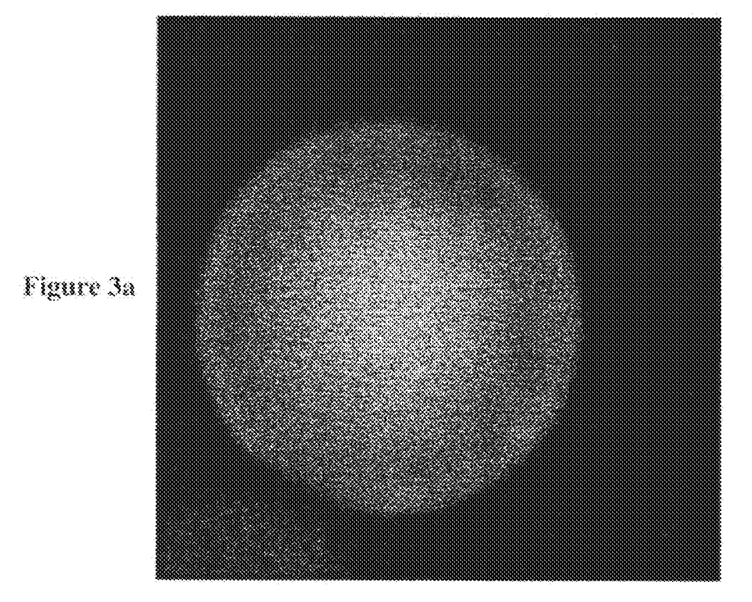
FIGS. 3a and 3b illustrate confocal images of a middle plane of an FD148-dex-ma microsphere before (upper) and after bleaching (under) a stripe of 3 µm at approximately 10 µm under the surface of the microsphere.
Figure 3B:
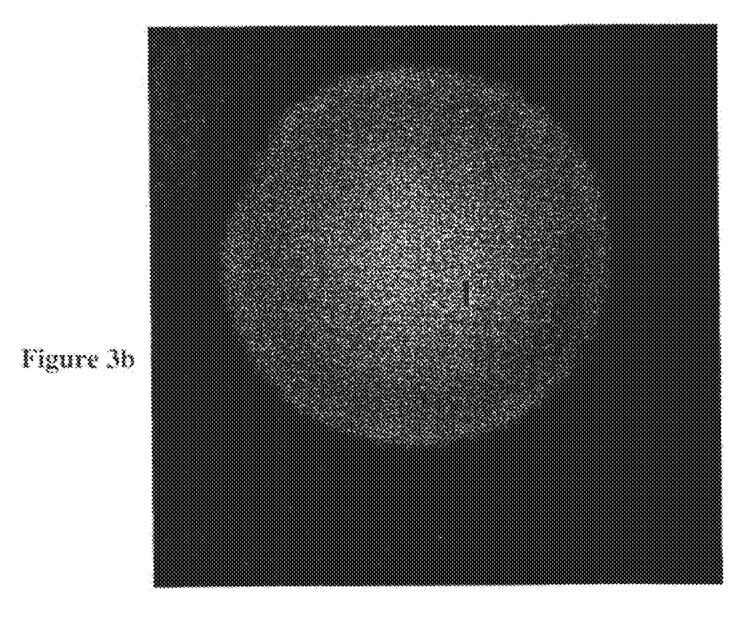
Figure 4:
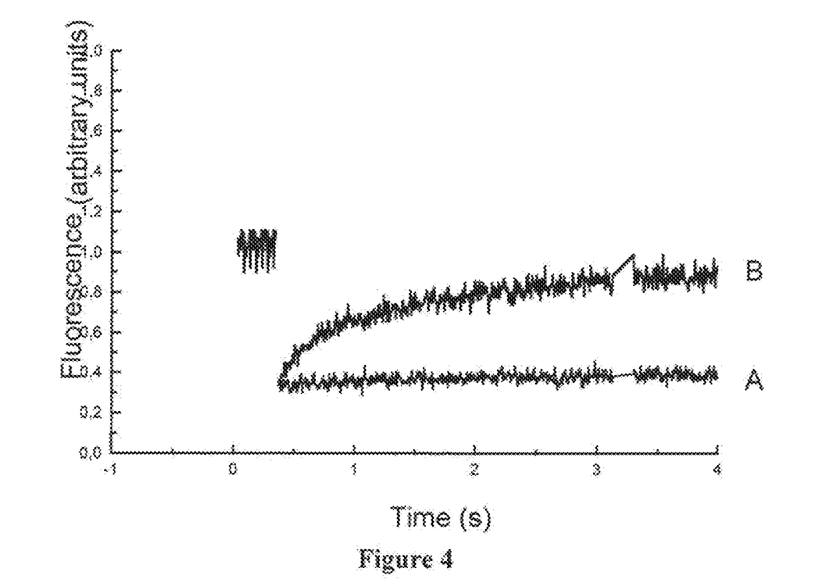
FIG. 4 illustrates fluorescence recovery curves of ED 148 in 148-dex-ma microspheres (A) and FITC in dex-ma microspheres loaded with FITC by submersion in a FITC solution (B).

FIGS. 3a and 3b shows the confocal images of a middle plane in an FD148-dex-ma microsphere respectively before and 2 minutes after bleaching the 3 μm segment. The diameter of the microsphere is approximately 25 μm. The latter image shows the bleach spot remains black indicating that, after 2 minutes, no fluorescence recovery occurred in the bleached region of the microsphere. FIG. 4 (curve A) shows the fluorescence in the bleached segment of this experiment did not recover, which allowed us to conclude that within the time scale of the experiment, the "large" FD148 chains were completely immobilized in the region of the dex-ma microsphere under investigation.

While FD148 chains could be sterically entrapped in the dex-ma polymer network as they were present during the formation of the microspheres, this could not occur for small FITC molecules when loaded into dex-ma microspheres by submersion of the fully polymerized dex-ma spheres into a FITCC solution. In this case, a complete fluorescence recovery was expected and experimentally confirmed. FIG. 4 (curve B) shows that FITC molecules located around 10 μm under the surface of the microsphere remain mobile.

Figure 5:
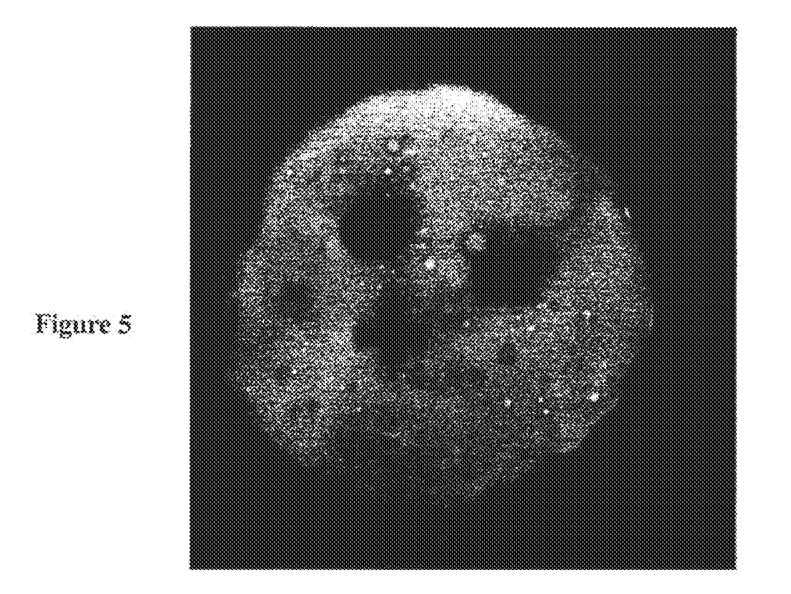
FIG. 5 illustrates a confocal image of a middle plane of an FD 148-dex-ma microsphere after bleaching an arbitrary geometry by SCAMP.

Besides the technical ability of photobleaching small segments in a sample, using scanning microscopes is straightforward to specifically select the microregions in the sample where bleaching has to occur as the laser beam can be locally positioned. Moreover, as the length, position as well as the number of segments are freely selectable in SCAMP experiments, any kind of geometry in the sample can be photobleached. FIG. 5 shows the confocal image in a middle plane of an FD148-dex-ma microsphere 2 minutes after bleaching a cross, a circle and a rectangle in the microspheres.

Example 3

SCAMP experiments were also performed on 45 μm FITC labeled latex beads purchased from PolylaB in Antwerp, Belgium. SCAMP was installed on a Bio-Rad MRC1024 CSLM following the work of Wedekind et al. (1994) and Wedekind et al. (1996). A 100× objective and a powerful argon laser (Spectra Physics 2017), used for obtaining sufficient photobleaching during the extremely short photobleaching times, were used in the SCAMP experiments on the 45 μm FITC labeled latex beads. The intensity of the Spectra Physics laser was installed at 300 mW, which resulted into a monitoring and photobleaching laser intensity of respectively 75 W and 20 mW (measured at the end of the optic fiber which launches the laser beam into the confocal scanning laser microscope). Consequently the ratio between monitoring and photobleaching laser intensity equaled 1:266. The wavelength of the laser beam, also during bleaching, was 488 nm.

SCAMP measurements were performed in the middle plane of the 45 μm FITC labeled latex beads. It occurred as follows. First, the image was zoomed in until the latex bead totally covered the picture. Second, the label of interest was defined and, by SCAMP software, it was indicated where the label had to be bleached on the latex bead. The labeling occurred at the time the laser beam scanned over the middle plane of the 45 μm FITC labeled latex beads. A temporarily strong increase in the intensity of the laser beam (from 75 W to 20 mW) occurred when the laser beam scanned over the segments that had to be bleached to create the label of interest. As the scan equaled 6 ms per "x-line" (FIG. 1A) and as one image of the confocal plane (i.e. the middle plane of the latex bead) consists of 512 "x-lines" it took 3.072 seconds to label a latex bead.

Figure 7:
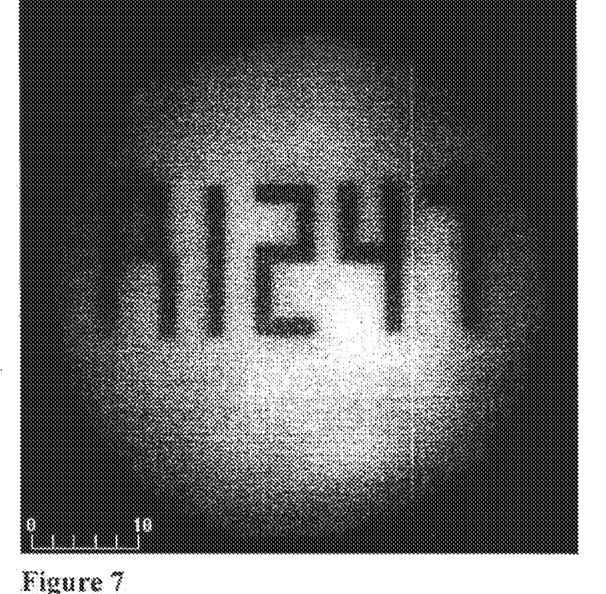
FIG. 7 illustrates a confocal image of the middle plane in a 45-µm FITC-labeled latex bead one hour after bleaching of the code R1247.
Figure 8:
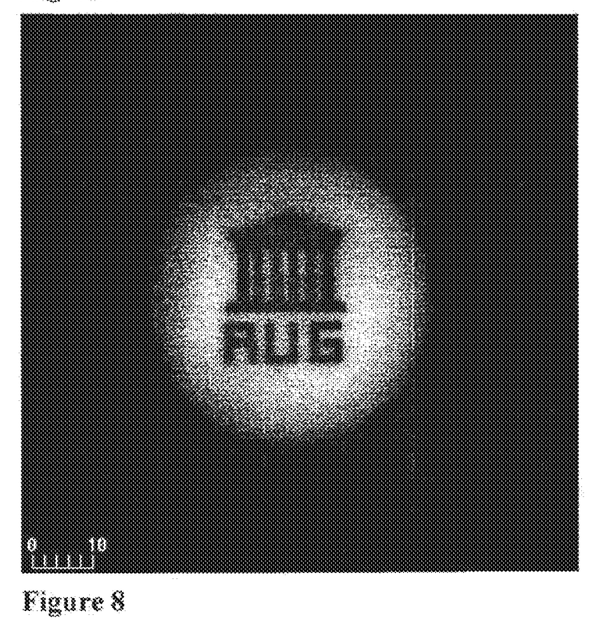
FIG. 8 illustrates a confocal image of the middle plane in a 45-µm FITC-labeled latex bead one hour after bleaching of the logo of Ghent University.
Figure 9:
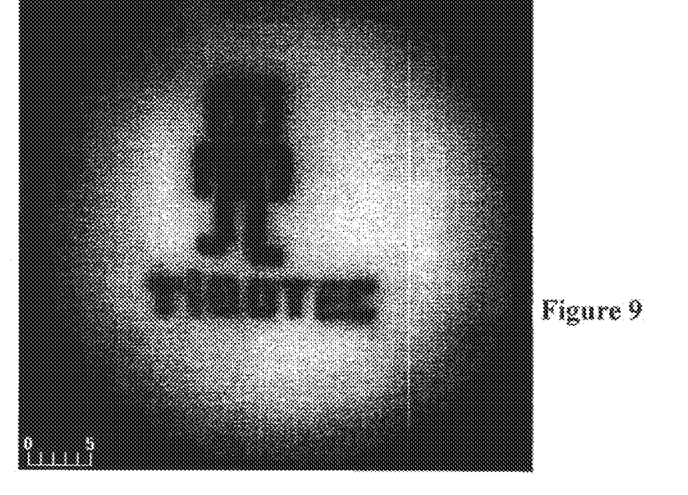
FIG. 9 illustrates a confocal image of the middle plane in a 45 µm FITC-labeled latex bead one hour after bleaching of the logo of the Tibotec company.

FIGS. 6 to 9 show the confocal images of a middle plane in the 45 μm FITC labeled latex beads one hour after bleaching of a barcode (FIG. 6a), a barcode plus number (FIG. 6b), the number R1247 (FIG. 7), the logo of Ghent University (FIG. 8) and the logo of Tibotec Company (FIG. 9). The images show the bleached segments remain black indicating that no significant fluorescence recovery occurred in the bleached segments of the latex beads.

Figure 6A:
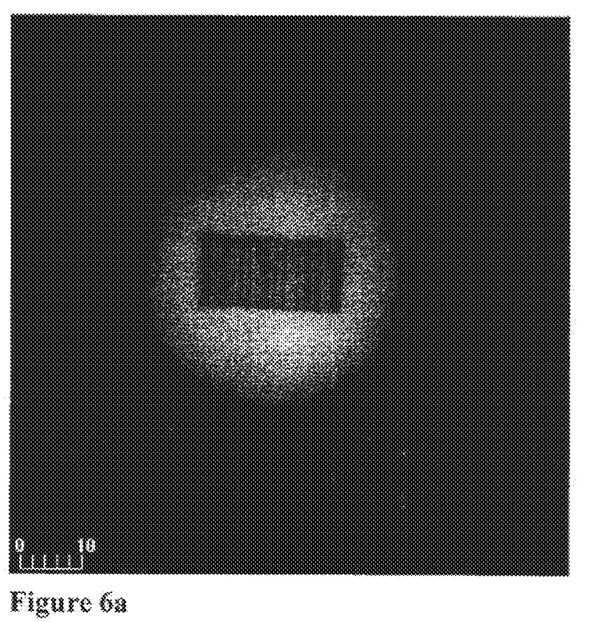
FIGS. 6a and 6b illustrate confocal images of the middle plane in a 45 µm FITC-labeled latex bead one hour after bleaching of a barcode (FIG. 6a) and barcode plus number (FIG. 6b).
Figure 6B:
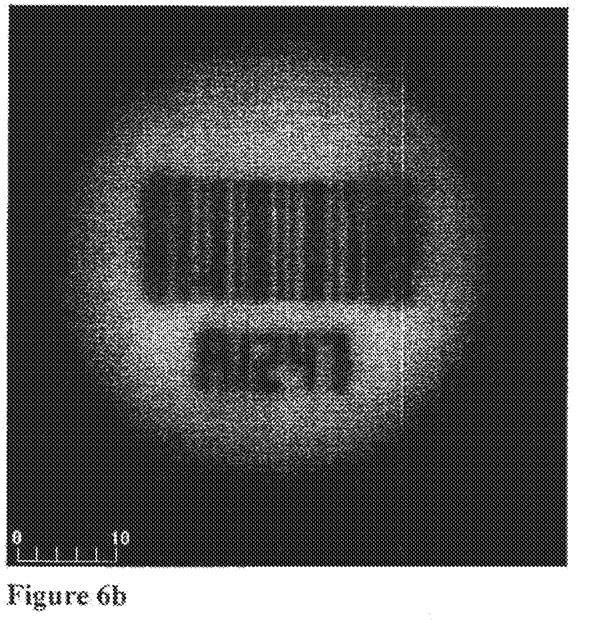

The values of the zoom option of the Bio-Rad MRC1024 confocal scanning laser microscope were as follows: 1.61 in FIG. 6a, 1.00 in FIG. 6b, 3.07 in FIG. 7, 1.00 in FIG. 8 and 1.00 in FIG. 9. The high spatial resolution of SCAMP to bleach labels is observed in FIGS. 6a and 6b. The label in FIG. 6a is composed of 3 different line types: one with a large width (2.5 μm), one with a medium width (1.25 μm) and one with a small width (0.62 μm). All lines are positioned at 1.25 μm from each other.

Example 4

The following experiments demonstrate methods for bleaching codes in fluorescent microcarriers, where the codes contain different levels of intensity due to different degrees of bleaching. The microcarriers used in the following experiments were 45 μm FITC labeled latex beads purchased from PolylaB in Antwerp, Belgium.

Figure 10:
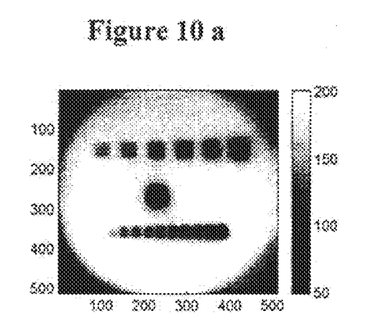

For one set of bleaching experiments, a 60× magnification and 300 mW laser power were used to produce the patterns shown in FIG. 10a. The squares in the top row of the figure have a breadth of 32 pixels (=2.46 μm) in the software and are separated by another 32 pixels. Bleaching enlarged them in reality. The squares in the bottom row of the figure are half thii size.

As shown in FIG. 10a, the bleaching of several intensities is possible. Assuming, for example, a plateau-level of 200 analog to digital units ("ADU"), bleaching is possible from at least levels 50 to 200 ADU approximately. Therefore, levels can be bleached over an interval of about 25% of the original fluorescent intensity. The photograph of FIG. 10a reveals that, for example, 6 levels of bleaching are certainly possible. Those six levels of bleaching are apparent from the six squares bleached in the top row of FIG. 10a. The fluorescent intensities of those squares are shown in the graph of FIG. 10c. The six squares of different fluorescent intensity were obtained by repeated bleaching (1 to 6 times). Using six coding sites having six different levels of fluorescent intensity allows for $6^6$, or 46656 different codes.

The series of the ten smaller bleached squares shown in FIG. 10a reveals clearly that bleaching by repeated scanning is not linear. These squares are only half as broad as the previous ones, but remain clearly distinguishable. The intensity levels for those markings are shown in the graph of FIG. 10d. Lastly, the intensity of a single bleach spot between the two rows of six and ten coding sites is shown in FIG. 10b.

Figure 11:
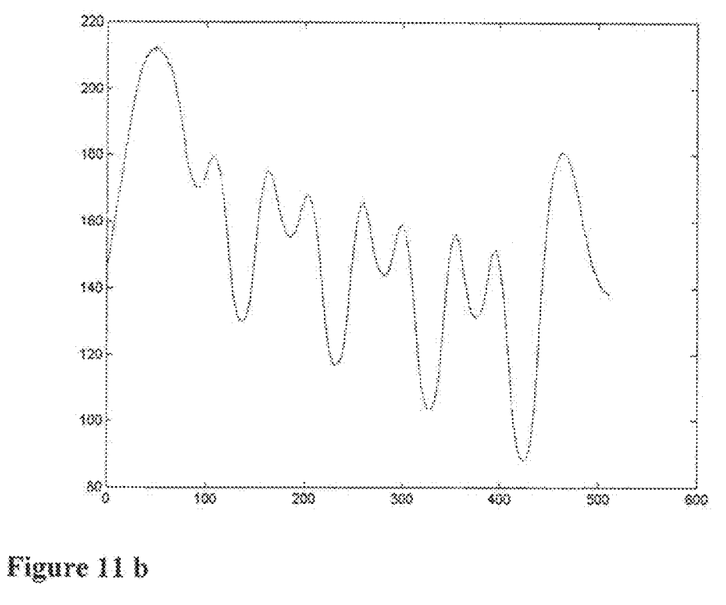
Figure 11A:
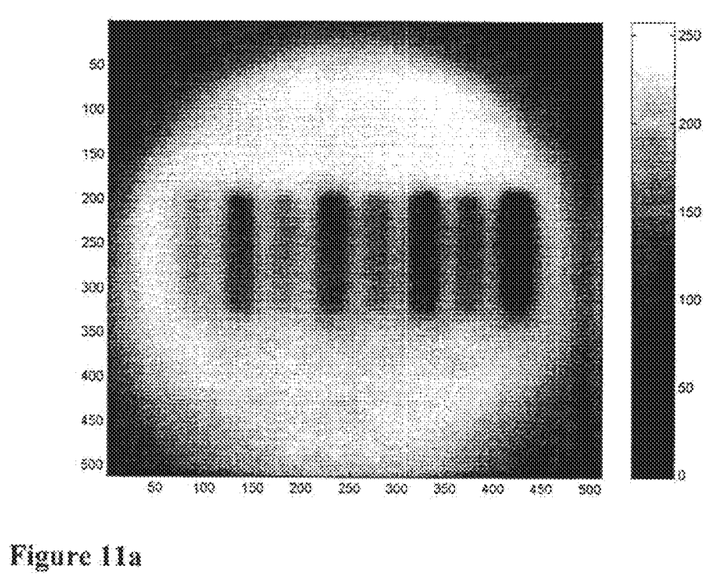

A second experiment was conducted to bleach a code effectively with 8 coding sites (software-breadth of 1 bar=24 pix×0.069 μm/pix=1.66 μm; separated by another 24 pixels) and 8 different intensities (allowing for $8^8$=16777216 different codes). The laser output was selected to be 200 mW. The photograph of the microcarrier of this experiment is illustrated in FIG. 11a, and the graph indicating the different intensity levels of the individual codes is shown in FIG. 11b.

The different intensities are clearly visible. This code of FIG. 11a is the number 1 5 2 6 3 7 4 8.

Figure 12:
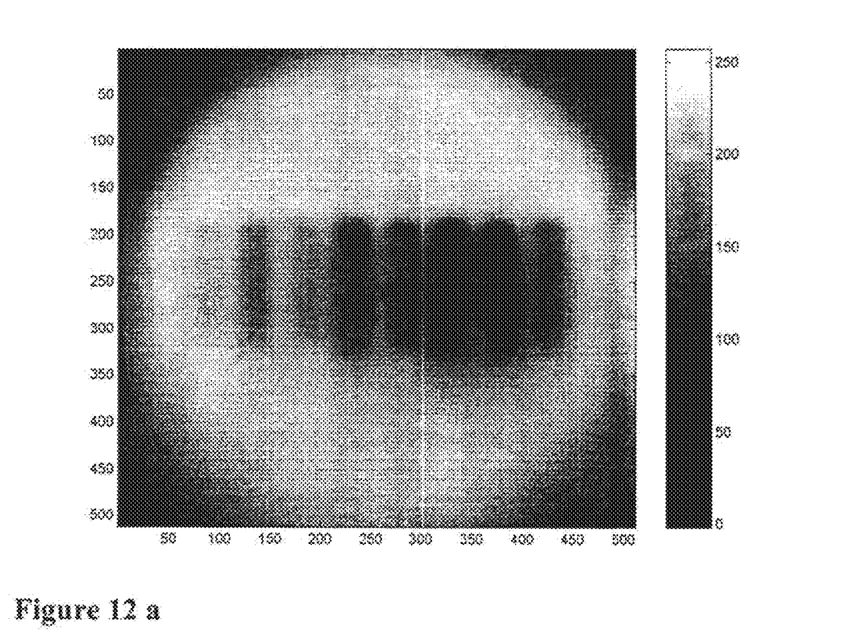

FIGS. 12a and 12b illustrate another example of eight encoding sites having eight different intensities. In this case, bleaching was performed with 250 mW instead of 200 mW as in the previous case, and was performed using 0.056 mm/pix. The code in this example was 1 3 2 6 5 8 7 4. The photograph of the codes, and a graph of the different intensities of the codes, is shown in FIGS. 12a and 12b, respectively.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of encoding and using microcarriers that serve as supports for ligands, wherein the microcarriers are spherical, cylindrical or oval in shape, said method comprising:
   chemically etching each of the microcarriers to write a code on a surface of each microcarrier or at an internal depth thereof, said code identifying the microcarrier;
   selecting a plurality of ligands, wherein each ligand binds or reacts with one or more target analytes;
   binding at least one of said plurality of ligands to the surface of each microcarrier;
   correlating the identity of the ligands with the codes of the microcarriers to which the ligands are bound;
   contacting the ligand-bound microcarriers with the one or more target analytes;
   observing any microcarriers upon which the one or more target analytes has bound or reacted with the microcarrier-bound ligands, and
   reading the codes of the microcarriers upon which the one or more target analytes has bound or reacted with the microcarrier-bound ligands; and
   using the correlation between the codes of the microcarriers and the identity of the ligands to identify any ligands with which the one or more target analytes have reacted, thereby determining presence or absence of the one or more target analytes.

2. A method as claimed in claim 1, wherein the step of chemically etching includes writing the code at a center plane of each microcarrier.

3. A method as claimed in claim 1, wherein said code takes the form of at least one number, letter, symbol, picture, bar code, ring code, or three-dimensional code.

4. A method as claimed in claim 1, wherein the one or more target analytes include a nucleic acid.

5. A method as claimed in claim 4, wherein at least one microcarrier-bound ligand is a reverse complement of said nucleic acid.

6. A method as claimed in claim 5, wherein the method involves DNA hybridization.

7. A method as claimed in claim 1, wherein the one or more target analytes are selected from the group consisting of the following:
   antigens, antibodies, receptors, haptens, enzymes, proteins, peptides, nucleic acids, drugs, hormones, pathogens, and toxins.

8. A method as claimed in claim 1, wherein the presence or absence of the one or more target analytes is indicated by a luminometric response.

9. A method as claimed in claim 1, wherein the microcarriers take the form of a sphere having a diameter of 1 to 200 µm.

10. A method as claimed in claim 1, wherein the microcarriers take the form of a bead.

11. A method as claimed in claim 1, wherein the codes of the microcarriers are read using a confocal microscope.

* * * * *